United States Patent [19]

Küle et al.

[11] Patent Number: 4,874,874

[45] Date of Patent: Oct. 17, 1989

[54] PREPARATION OF 3-SULPHENYLMALEIMIDES

[75] Inventors: Engelbert Küle, Bergisch Gladbach; Alfons Adler, Cologne, both of Fed. Rep. of Germany

[73] Assignee: Bayer Aktiengesellschaft, Leverkusen, Fed. Rep. of Germany

[21] Appl. No.: 113,688

[22] Filed: Oct. 26, 1987

[30] Foreign Application Priority Data

Nov. 4, 1986 [DE] Fed. Rep. of Germany ....... 3637507

[51] Int. Cl.[4] .......................................... C07D 207/456
[52] U.S. Cl. .................................................... 548/544
[58] Field of Search ........................................ 548/544

[56] References Cited

U.S. PATENT DOCUMENTS

| | | | |
|---|---|---|---|
| 3,184,475 | 5/1965 | Eby et al. | 548/544 |
| 3,224,936 | 12/1965 | Prill et al. | 167/30 |
| 4,364,958 | 12/1982 | Seres et al. | 548/544 |
| 4,520,206 | 5/1985 | Happ | 548/548 |

FOREIGN PATENT DOCUMENTS

| | | | |
|---|---|---|---|
| 2143601 | 3/1972 | Fed. Rep. of Germany . | |
| 0076122 | 9/1970 | German Democratic Rep. . | |
| 0569568 | 8/1977 | U.S.S.R. | 548/548 |

OTHER PUBLICATIONS

IX. On the Antifungal Activity of Various Malemmide and Succinimide Compounds; *Abstract in Zusammenhang mit Chemical Substance Index. O-P, Band 102, Januar-Juni, 1985, Seite 6891CS, Spalte 1: 1-(3-chlorophenyl)-3-(ethylthio) 1-H-pyrrole-2,5-dione und 1-(-3-chlorophy)-3-[(1-methylethyl)thio]-1 H-pyrrole-2,-5-dione* GB-A-2 054 589 . . . ; Houben-Weyl "Methoden der Organischen Chemie".
Polymer Preprints, Band 26, Nr. 1, 1985, Seiten 132-133; J. E. White, "Step-Growth Polymers from Bismalemides. Synthesis and Reactions of Some New Polyimides"*Seite 133, Tabelle III.
Seite 132, Spalte 2, G1.4*; Chemical Abstracts, band 102, Nr. 15, Apr. 15, 1985, Seite 16, Spaletel, U.S.; S.

Matsui et al.: "Studies on the Experimental Chemotherapy for Dermatomycosis and Candidiasis."

*Primary Examiner*—David B. Springer
*Attorney, Agent, or Firm*—Sprung Horn Kramer & Woods

[57] ABSTRACT

A process for the preparation of a 3-sulphenylmaleimide of the formula

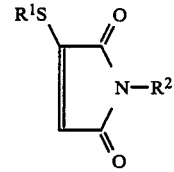

in which
$R^1$ is alkyl, or optionally substituted cycloalkyl or aralkyl, and
$R^2$ is optionally substituted alkyl, cycloalkyl, aryl or aralkyl,
comprising reacting a 3-sulphenylsuccinimide of the formula

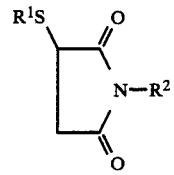

with an equimolar amount of hydrogen peroxide in the presence of a lower alkanecarboxylic acid. The compounds are fungicidal and those are new where $R^2$ is not alkyl, or where $R^1$ is not alkyl while $R^2$ is optionally substituted phenyl.

4 Claims, No Drawings

PREPARATION OF 3-SULPHENYLMALEIMIDES

The present invention relates to a new process for the preparation of 3-sulphenylmaleimides, some of which are new, and their use as agents for combating pests.

It is known that 3 sulphenylmaleimides are obtained by reacting 3-chloromaleimides with mercaptans, if appropriate in the form of alkali metal salts and it appropriate in the presence of solvents (compare East German Patent 76,122 and DOS (German Published Specification) 2,143,601). The process has the disadvantage that the starting materials to be used - the 3-chloromaleimides - are obtained in two stages from maleimides and chlorine via the corresponding dichlorosuccinic acid derivatives by splitting off hydrogen chloride.

It is furthermore known that 3 sulphenylmaleimides are obtained by reacting sulphenyl chlorides with maleimides. The starting compounds—the sulphenyl chlorides—are obtained from mercaptans by chlorination. The yield of the end stage is only 42% of a still impure product (compare, for example, U.S. Pat. Nos. 3,184,475 and 3,224,936).

It has now been found that the 3-sulphenylmaleimides of the general formula (I)

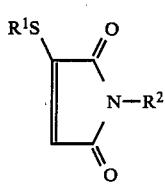

in which $R^1$ represents alkyl, or represents optionally mono- or polysubstituted cycloalkyl, or represents optionally mono- or polysubstituted aralkyl and $R^2$ represents optionally mono- or polysubstituted alkyl, or represents optionally mono- or polysubstituted cycloalkyl, or represents optionally mono- or polysubstituted aryl, or represents optionally mono- or polysubstituted aralkyl, are obtained by a new process in which 3-sulphenylsuccinimides of the general formula (II)

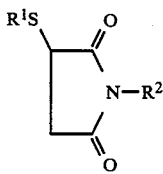

in which $R^1$ and $R^2$ have the abovementioned meanings, are reacted with hydrogen peroxide in a molar ratio of 1:1 in the presence of a lower alkanecarboxylic acid as the solvent, at temperatures between 20° C. and 120° C.

Preferably, in formula (I), $R^1$ represents straight-chain or branched alkyl with 1 to 12 carbon atoms, or represents cycloalkyl which has 5 to 10 carbon atoms and is optionally mono- or polysubstituted by identical or different substituents, or represents aralkyl which has 6 to 10 carbon atoms in the aryl part and optionally 1 to 4 carbon atoms in the alkyl part and is optionally mono- or polysubstituted by identical or different substituents, substituents in the aryl which may be mentioned being: halogen, alkyl or alkoxy with 1 to 4 carbon atoms, alkylthio with 1 to 4 carbon atoms, halogenoalkyl, halogenoalkoxy and halogenoalkylthio with in each case 1 to 3 carbon atoms and 1 to 5 halogen atoms and nitro; and $R^2$ represents straight-chain or branched alkyl with 1 to 12 carbon atoms, or represents cycloalkyl which has 5 to 10 carbon atoms and is optionally mono- or polysubstituted by identical or different substituents, or represents aralkyl which has 6 to 10 carbon atoms in the aryl part and 1 to 4 carbon atoms in the alkyl part and is optionally mono- or polysubstituted by identical or different substituents, or represents aryl which has 6 to 10 carbon atoms and is optionally mono- or polysubstituted by identical or different substituents, substituents in the aryl part of the aralkyl or in the aryl itself which may be mentioned being: halogen, alkyl with 1 to 4 carbon atoms, alkoxy with 1 to 4 carbon atoms, alkylthio with 1 to 4 carbon atoms, halogenoalkyl, halogenoalkoxy and halogenoalkylthio with in each case 1 to 3 carbon atoms and 1 to 5 halogen atoms and nitro.

Particularly preferably, in formula (I)

$R^1$ represents straight-chain or branched alkyl with 1 to 8 carbon atoms, or represents cycloalkyl which has 5 to 8 carbon atoms and is optionally mono-, di-, tri- or tetrasubstituted by alkyl with 1 to 4 carbon atoms, or represents phenylalkyl which has 1 to 3 carbon atoms in the alkyl part and is optionally mono-, di-, tri-, tetra- or pentasubstituted by identical or different substituents, substituents in the phenyl which may be mentioned being: fluorine, chlorine, alkyl with 1 to 3 carbon atoms, alkoxy with 1 to 3 carbon atoms, alkylthio with 1 to 3 carbon atoms, halogenoalkyl, halogenoalkoxy and halogenoalkylthio with in each case 1 or 2 carbon atoms and 1 to 3 identical or different halogen atoms, such as fluorine and chlorine, and nitro and $R^2$ represents straight-chain or branched alkyl with 1 to 8 carbon atoms, or represents cycloalkyl which has 5 to 8 carbon atoms and is optionally mono-, di-, tri- or tetrasubstituted by alkyl with 1 to 4 carbon atoms, or represents phenylalkyl which has 1 to 3 carbon atoms in the alkyl part and is optionally mono-, di-, tri-, tetra- or pentasubstituted by identical or different substituents, or represents phenyl which is mono-, di-, tri-, tetra- or pentasubstituted by identical or different substituents, substituents of the phenyl and in the phenyl of the phenylalkyl which may be mentioned being: fluorine, chlorine, alkyl or alkoxy with 1 to 3 carbon atoms, alkylthio with 1 to 3 carbon atoms, halogenoalkyl, halogenoalkoxy and halogenoalkylthio with in each case 1 or 2 carbon atoms and 1 to 3 identical or different halogen atoms, such as fluorine and chlorine, and nitro.

Especially preferably, in formula (I)

$R_1$ represents straight-chain or branched alkyl with 1 to 5 carbon atoms, or represents cyclohexyl, and $R^2$ represents straight-chain or branched alkyl with 1 to 5 carbon atoms, or represents cyclohexyl, or represents phenyl, benzyl or phenethyl, in each case optionally mono-, di- or trisubstituted by identical or different substituents, substituents which may be mentioned being: chlorine, methyl, ethyl, trifluoromethyl, trifluoromethoxy, trifluoromethylthio, chlorodifluoromethoxy, 2-chloro1,1-difluoroethoxy and nitro.

It is to be described as decidedly surprising that, in the reaction according to the invention of 3-sulphenylsuccinimides of the formula (II) with 1 mole of hydrogen peroxide, the compounds of the formula (I), some of which are new, can be obtained in such good yields and such a high purity, because in view of the prior art it had to be expected that the reaction leads to a mixture of different products, since it has been known for a long time that 3-sulphenylsuccinimides are oxidized with excess hydrogen peroxide to give 3-sulphonylsuccinimides (compare, for example, DOS (German Published Specification) 2,143,601 and DOS (German Published Specification) 3,026,755).

The process according to the invention has a number of advantages. Thus, the end products are obtained in high purity and in good yields in a simple one-stage reaction, it also being possible for the starting compounds of the formula (II) required to be prepared in a one-stage process in a simple smooth manner.

If 3-n-butylsulphenyl-1-phenyl-succinimide is used as the starting compound and this is reacted with 1 mole of 35% strength hydrogen peroxide, the course of the process according to the invention can be illustrated by the following equation:

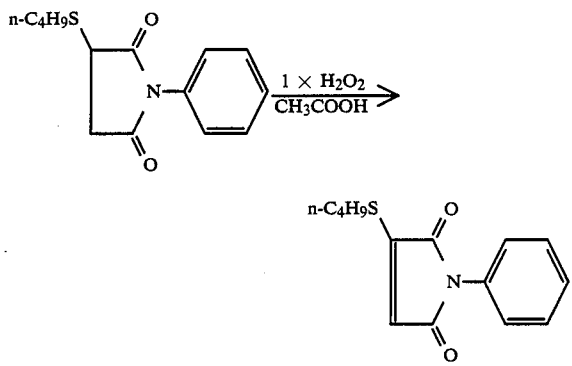

Formula (II) provides a general definition of the 3-sulphenylsuccinimides required as starting substances in the process according to the invention. In this formula, $R^1$ and $R^2$ have those meanings which have already been mentioned for these radicals in connection with the description of the process according to the invention for the compounds of the formula (I).

The following compounds may be mentioned as examples of 3-sulphenylsuccinimides: 3-methylsulphenylsuccinimide substituted on the nitrogen by methyl, butyl, tert.-butyl, cyclopentyl, cyclohexyl, benzyl, 4-trifluoromethylbenzyl, 4-trifluoromethoxybenzyl, phenyl, 4-tolyl-, 4-chlorophenyl, 3-nitrophenyl, 3,4-dichlorophenyl, 3-trifluoromethylphenyl; 4-trifluoromethylphenyl or 4-trifluoromethylthiophenyl.

3-isopropylsulphenylsuccinimide substituted on the nitrogen by isopropyl, isooctyl, dodecyl, 3,3,5-trimethylcyclohexyl, 2-phenethyl, 2-tolyl, 2,4-dichlorophenyl, 2,6-dimethylphenyl, 3-trifluoromethylphenyl or 4-(2-chloro-1,2,2-trifluoroethoxy)-phenyl;

3-N-butylsulphenylsuccinimide substituted on the nitrogen by methyl, isobutyl, cyclohexyl, 4-chlorobenzyl, phenyl, 2-chlorophenyl, 2-nitrophenyl or 2,6-diethylphenyl 3-cyclohexylsulphenylsuccinimide substituted on the nitrogen by methyl, neopentyl, cyclohexyl, phenyl or 2-trifluoromethoxyphenyl.

The 3-sulphenylsuccinimides are known in some cases.

They can be prepared, for example, (1) by addition of thiols onto N-substituted maleimides (compare DOS (German Published Specification) 3,026,755) or (2) by cyclization of a 3-sulphenylsuccinic acid monoamide with dehydration (compare DOS (German Published Specification) 2,143,601). Reference is also made to the preparation examples.

The hydrogen peroxide also required is a commercial product which can be prepared on a large industrial scale.

Possible diluents or solvents for the process according to the invention are lower alkanecarboxylic acids. These include, preferably, formic acid, acetic acid and propionic acid, which can optionally also contain water.

The reaction is carried out at temperatures between 20° C. and 120° C., preferably between 80° C. and 120° C.

The reaction is usually carried out under normal pressure.

The starting compounds of the formula (II) are reacted with the hydrogen peroxide in a molar ratio of 1:1.

In carrying out the process according to the invention, the 3-sulphenylsuccinimide is in general initially introduced into the lower alkanoic acid and the hydrogen peroxide is added dropwise in the stated temperature range. To bring the reaction to completion, the mixture is preferably after-heated for a few minutes and cooled and the desired product is precipitated by addition of water and, after filtration with suction and drying, is usually already present in a high purity so that recrystallization is unnecessary.

The compounds which can be prepared by the process according to the invention and their use are known in some cases.

Thus, it is known that 3-sulphenylmaleimides, such as 3-ethylsulphenyl-1-phenyl-maleimide, are useful as leaf fungicides, as seed dressing agents and for preservation of various materials (compare East German Patent 76,122). It is furthermore known that 3-phenylsulphenyl1-alkyl-maleimides have an action against bacteria and fungi (compare U.S. Pat. No. 3,224,936). 3-Alkylsulphenyl- and 3-phenylsulphenyl-1-phenylmaleimides are also known for use in the preservation of materials (compare Japanese Pat. No. 53,032,119).

It has been found that the use of the compounds of the formula (IA).

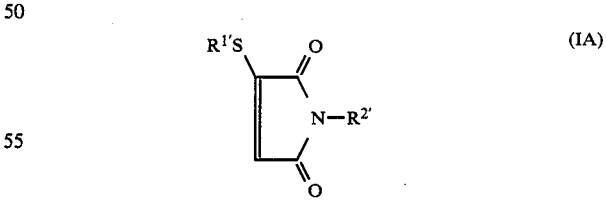

in which $R^{1'}$ represents alkyl, or represents optionally mono- or polysubstituted cycloalkyl, or represents optionally mono- or polysubstituted aralkyl and $R^{2'}$ represents optionally mono- or polysubstituted alkyl, or represents optionally mono- or polysubstituted cycloalkyl, or represents optionally mono- or polysubstituted aryl, or represents optionally mono- or polysubstituted aralkyl, excluding the compound 3-ethylsulphenyl-1-phenylmaleimide, as fungicides in plant protection is new and is part of the invention.

Surprisingly, the 3-sulphenylmaleimides of the formula (IA) have a better fungicidal action than the compounds which are similar structurally and from the point of view of their action and are known from the prior art.

Preferably, in formula (IA), $R^{1'}$ represents straight-chain or branched alkyl with 1 to 12 carbon atoms, or represents cycloalkyl which has 5 to 10 carbon atoms and is optionally mono-, di-, tri- or tetrasubstituted by alkyl with 1 to 4 carbon atoms, or represents aralkyl which has 6 to 10 carbon atoms in the aryl part and 1 to 4 carbon atoms in the alkyl part and is optionally mono- or polysubstituted by identical or different substituents, substituents in the aryl which may be mentioned being: halogen, alkyl with 1 to 4 carbon atoms, alkoxy with 1 to 4 carbon atoms, alkylthio with 1 to 4 carbon atoms, halogenoalkyl, halogenoalkoxy and halogenoalkylthio with in each case 1 to 3 carbon atoms and 1 to 5 halogen atoms and nitro; and $R^{1'}$ represents straight-chain or branched alkyl with 1 to 12 carbon atoms, or represents cycloalkyl which has 5 to 10 carbon atoms and is optionally mono-, di-, tri- or tetrasubstituted by alkyl with 1 to 4 carbon atoms, or represents aralkyl which has 6 to 10 carbon atoms in the aryl part and 1 to 4 carbon atoms in the alkyl part and is optionally mono- or polysubstituted by identical or different substituents, or represents aryl which has 6 to 10 carbon atoms and is optionally mono- or polysubstituted by identical or different substituents, substituents in the aryl part of the aralkyl or in eh aryl itself which may be mentioned being: halogen, alkyl with 1 to 4 carbon atoms, alkoxy with 1 to 4 carbon atoms alkylthio with 1 to 4 carbon atoms, halogenoalkyl, halogenoalkoxy and halogenoalkylthio with in each case 1 to 3 carbon atoms and 1 to 5 halogen atoms and nitro, excluding the compound 3-ethylsulphenyl-1-phenylmaleimide.

Particularly preferably, in formula (IA), $R^{1'}$ represents straight-chain or branched alkyl with 1 to 8 carbon atoms, or represents cycloalkyl with 5 to 8 carbon atoms, or represents phenylalkyl which has 1 to 3 carbon atoms in the alkyl part and is optionally mono-, di-, tri-, tetra- or pentasubstituted by identical or different substituents, substituents which may be mentioned being: fluorine, chlorine, alkyl with 1 to 3 carbon atoms, alkoxy with 1 to 3 carbon atoms, alkylthio with 1 to 3 carbon atoms, halogenoalkyl, halogenoalkoxy and halogenoalkylthio with in each case 1 or 2 carbon atoms and 1 to 3 identical or different halogen atoms, such as fluorine and chlorine, and nitro and $R^{2'}$ represents straight-chain or branched alkyl with 1 to 8 carbon atoms, or represents cycloalkyl with 5 to 8 carbon atoms, or represents phenylalkyl which has 1 to 3 carbon atoms in the alkyl part and is optionally mono-, di-, tri-, tetra- or pentasubstituted by identical or different substituents, or represents phenyl which is mono-, di-, tri-, tetra- or pentasubstituted by identical or different substituents, substituents of the phenyl and in the phenyl of the phenylalkyl which may be mentioned being: fluorine, chlorine, alkyl or alkoxy with 1 to 3 carbon atoms, alkylthio with 1 to 3 carbon atoms, halogenoalkyl, halogenoalkoxy and halogenoalkylthio with in each case 1 or 2 carbon atoms and 1 to 3 identical or different halogen atoms, such as fluorine and chlorine, and nitro; excluding the compound 3-ethylsulphenyl-1-phenylmaleimide.

Especially preferably, in formula (IA), $R^{1'}$ represents straight-chain or branched alkyl with 1 to 5 carbon atoms, or represents cyclohexyl, and $R^{2'}$ represents straight-chain or branched alkyl with 1 to 5 carbon atoms, or represents cyclohexyl, or represents phenyl, benzyl or phenethyl which is optionally mono-, di- or trisubstituted by identical or different substituents, substituents which may be mentioned being: chlorine, methyl, ethyl, trifluoromethyl, trifluoromethoxy, trifluoromethylthio, chlorodifluoromethoxy, 2-chloro-1,1-difluoroethoxy and nitro;

excluding the compound 3-ethylsulphenyl-1-phenylmaleimide.

It has furthermore been found that the 3-sulphenylmaleimides obtainable by the process according to the invention, of the formula (IB)

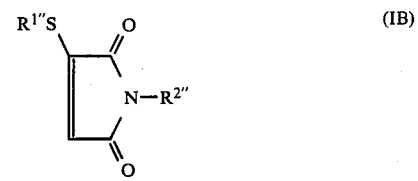

in which $R^{1''}$ represents alkyl, or represents optionally substituted cycloalkyl, or represents optionally substituted aralkyl and $R^{2''}$ represents optionally substituted cycloalkyl, or represents optionally substituted aralkyl, or represents substituted aryl, excluding the compounds in which $R^{1''}$ represents alkyl and $R^{2''}$ represents phenyl which is unsubstituted or substituted by halogen, alkyl or alkoxy, are new.

Preferably, in formula (IB), $R^{1''}$ represents straight-chain or branched alkyl with 1 to 12 carbon atoms, or represents cycloalkyl which has 5 to 10 carbon atoms and is optionally mono-, di-, tri- or tetrasubstituted by alkyl with 1 to 4 carbon atoms, or represents aralkyl which has 6 to 10 carbon atoms in the aryl part and 1 to 4 carbon atoms in the alkyl part and is optionally mono- or polysubstituted by identical or different substituents, substituents in the aryl which may be mentioned being: halogen, alkyl with 1 to 4 carbon atoms, alkoxy with 1 to 4 carbon atoms, halogenoalkyl, halogenoalkoxy and halogenoalkylthio with in each case 1 to 3 carbon atoms and 1 to 5 halogen atoms and nitro; and $R^{2''}$ represents cycloalkyl which has 5 to 10 carbon atoms and is optionally mono-, di-, tri- or tetrasubstituted by alkyl with 1 to 4 carbon atoms, or represents aralkyl which has 6 to 10 carbon atoms in the aryl part and 1 to 4 carbon atoms in the alkyl part and is optionally mono- or polysubstituted by identical or different substituents, or represents aryl which has 6 to 10 carbon atoms and is optionally mono- or polysubstituted by identical or different substituents, substituents in the aryl part of the aralkyl or in the aryl itself which may be mentioned being: halogen, alkyl with 1 to 4 carbon atoms, alkoxy with 1 to 4 carbon atoms, alkylthio with 1 to 4 carbon atoms, halogenoalkyl, halogenoalkoxy and halogenoalkylthio with in each case 1 to 3 carbon atoms and 1 to 5 halogen atoms and nitro; excluding the compounds in which $R^{1''}$ represents alkyl and $R^{2''}$ represents phenyl which is unsubstituted or substituted by halogen, alkyl or alkoxy.

Particularly preferably, in formula (IB), $R^{1''}$ represents straight-chain or branched alkyl with 1 to 8 carbon atoms, or represents cycloalkyl with 5 to 8 carbon atoms, or represents phenylalkyl which has 1 to 3 carbon atoms in the alkyl part and is optionally mono-, di-, tri-, tetra- or pentasubstituted by identical or different substituents, substituents in the phenyl which may be mentioned being: fluorine, chlorine, alkyl with 1 to 3 carbon atoms, alkoxy with 1 to 3 carbon atoms, alkylthio with 1 to 3 carbon atoms, halogenoalkyl, halogenoalkoxy and halogenoalkylthio with in each case 1 or 2 carbon atoms and 1 to 3 identical or different halogen atoms, such as fluorine and chlorine, and nitro and $R^{2''}$ represents cycloalkyl with 5 to 8 carbon atoms, or represents phenylalkyl which has 1 to 3 carbon atoms in the alkyl part and is optionally mono-, di-, tri-, tetra- or pentasubstituted by identical or different substituents or represents phenyl which is mono-, di-, tri-, tetra- or pentasubstituted by identical or different substituents, substituents of the phenyl and in the phenyl of the phenylalkyl which may be mentioned being: fluorine, chlorine, alkyl with 1 to 3 carbon atoms, alkoxy with 1 to 3 carbon atoms, alkylthio with 1 to 3 carbon atoms, halogenoalkyl, halogenoalkoxy and halogenoalkylthio which in each case 1 or 2 carbon atoms and 1 to 3 identical or different halogen atoms, such as fluorine, chlorine, and nitro; excluding the compounds in which $R^{1''}$ represents alkyl and $R^{2''}$ represents phenyl which is unsubstituted or substituted by halogen, alkyl or alkoxy.

Especially preferably, in formula (IB), $R^{1''}$ represents straight-chain or branched alkyl with 1 to 5 carbon atoms, or represents cyclohexyl and $R^{2''}$ represents cyclohexyl, or represents benzyl or phenethyl which is optionally mono-, di- or trisubstituted by identical or different substituents, or represents substituted phenyl, substituents which may be mentioned being: chlorine, methyl ethyl, trifluoromethyl, trifluoromethoxy, trifluoromethylthio, chlorodifluoromethoxy, 2-chloro1,1-difluoroethoxy and nitro; excluding the compounds in which $R^{1''}$ represents alkyl and $R^{2''}$ represents phenyl which is substituted by halogen, alkyl or alkoxy.

The compounds of the formula (IA) and (IB) which can be prepared by the process according to the invention have a good biological action and can be used for combating pests. The active compounds are suitable for use, for example, as plant protection agents, above all as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation: Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubensis;* Plasmopara species, such as, for example, *Plasmopara viticola;* Peronospora species, such as, for example, *Peronospora psis* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, Uromyces appendiculatus; Puccinia species, such as, for example, *Puccinia recondita;* tilletia species, such as, for example Tilletia caries; Ustilago species, such as, for example, *Ustilago nuda* or *Ustilago avenae;* Pellicularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternatia brassicqe* and Pseudocercosporella species, such as, for example, *Pseudocercosporella herpotrichoides.*

The good toleration, by plants, of the active compounds, at the concentrations required for combating plant diseases, permits treatment of above-ground parts of plats, of vegetative propagation stock and seeds, and of the soil.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surfaceactive agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsuphoxide, as well as water. By liquified gaseous extenders or carriers are meant liquids which are gaseous at normal temperature and under normal pressure, for example aerosol propellants, such as halogenated hydrocarbons as well as butane, propane nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylenefatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.001 to 0.02% by weight, are required at the place of action.

PREPARATION EXAMPLES

Example 1

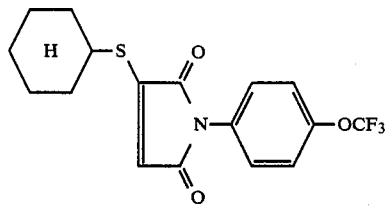

8 g (0.021 mol) of 3-cyclohexylsulphenyl-1-(4-trifluoromethoxyphenyl)-succinimide are dissolved in 100 ml of acetic acid. 2.1 ml (0.021 mol) of 35% strength aqueous hydrogen peroxide are added dropwise at 90° to 100° C. The mixture is heated at the boiling for 10 minutes and cooled and 200 ml of water are added. 3-Cyclohexylsulphenyl-1-(4-trifluoromethoxyphenyl)-maleimide thereby precipitates out. After filtration with suction and drying, 4 g (50% of theory) of 3-cyclohexylsulphenyl-1-(4-trifluoromethoxyphenyl)-maleimide of melting point 128° to 132° C. are obtained. The following 3-sulphenylmaleimides of the formula (I) are obtained in a similar manner.

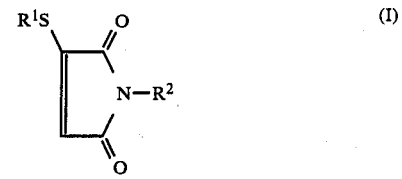

| No. | $R^1$ | $R^2$ | Yield [% of theory] | Physical data [melting point °C.; refractive index $n_D^{20}$] |
|---|---|---|---|---|
| 2 | i-$C_3H_7$ | 4-$CF_3O$—$C_6H_4$— | 67 | 112–114 |
| 3 | " | 4-$CF_3S$—$C_6H_4$— | 56 | 126–128 |
| 4 | " | 4-$CH_3$—$C_6H_4$— | 65 | 110–112 |
| 5 | " | 2,4-$Cl_2C_6H_3$— | 98 | 1.5072 |
| 6 | " | 2-$NO_2$—$C_6H_4$— | 97 | 1.5088 |
| 7 | " | 2-Cl—$C_6H_4$— | 70 | 1.5704 |
| 8 | " | 2-$CH_3$—$C_6H_4$— | 95 | 1.5651 |
| 9 | " | 3-$CH_3$—$C_6H_4$— | 98 | 1.5063 |
| 10 | " | $C_6H_5$—$CH_2$— | — | 71–73 |
| 11 | " | 3-$CF_3$—$C_6H_4$—$CH_2$ | — | 1.5302 |
| 12 | " | 3-Cl, 4-$CF_3$—$C_6H_3$—$CH_2$— | — | 1.5398 |
| 13 | n-$C_4H_9$ | 2,6-$(C_2H_5)_2$—$C_6H_3$— | 98 | 1.5464 |
| 14 | " | 4-$CF_3O$—$C_6H_4$— | 86 | 101–105 |
| 15 | " | 3,4-$Cl_2$—$C_6H_3$— | 83 | 105–107 |
| 16 | " | 2,4-$Cl_2$—$C_6H_3$— | 98 | 1.5389 |
| 17 | " | 2-Cl—$C_6H_4$— | 82 | 1.5631 |
| 18 | " | $C_6H_5$—$CH_2$— | — | 77–80 |
| 19 | " | 3-$CF_3$—$C_6H_4$—$CH_2$— | — | 1.5307 |
| 20 | $C_6H_{11}$ | 4-$CF_3$—$C_6H_4$— | 41 | 145–147 |
| 21 | " | 4-$CH_3$—$C_6H_4$— | 41 | 177–179 |
| 22 | " | 3-$ClCH_2$—$CF_2O$—$C_6H_4$— | 86 | 1.5590 |
| 23 | " | 2-$CF_3O$—$C_6H_4$— | 80 | 1.5363 |
| 24 | " | 4-$CF_3O$—$C_6H_4$— | 50 | 132 |
| 25 | " | 4-$CF_2ClO$—$C_6H_4$— | 67 | 117–121 |
| 26 | " | 3-Cl, 4-$CF_3O$—$C_6H_4$— | 40 | 132–134 |
| 27 | " | 2,4-$(CF_3)_2$—$C_6H_3$— | 94 | 1.5130 |
| 28 | " | 3-$CF_3O$—$C_6H_4$— | 72 | 95–97 |
| 29 | " | 2-$CF_3$—$C_6H_4$— | 30 | 1.5054 |
| 30 | i-$C_3H_7$ | $C_6H_{11}$ | 55 | 85 |
| 31 | " | i-$C_4H_9$— | 32 | 33 |

Preparation of the starting substances of the formula (II) Example A1

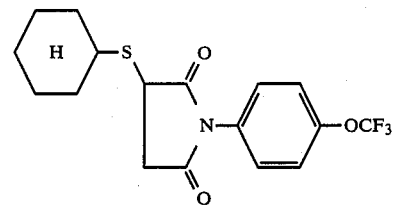

10.7 g (0.05 mol) of 3-cyclohexylsulphenylsuccinic acid anhydride are dissolved in 50 ml of toluene and a solution of 8.9 g (0.05 mol) of 4-trifluoromethoxyaniline in 50 ml of toluene is added dropwise. The temperature thereby rises to 42° C. The mixture is cooled, a little petroleum ether is added and the amide acid formed is filtered off with suction (melting point 137° to 139° C.; yield 16 g).

11 g of this amide acid are heated under reflux in 100 ml of xylene with the addition of 1 ml of concentrated sulphuric acid for 1 hour, using a water separator. After cooling, 250 ml of water are added, the small amount of undissolved material is separated off in vacuo. 10 g of 3-cyclohexylsulphenyl-1-(4-trifluoromethoxyphenyl)-succinimide of melting point 125° to 127° C. are obtained.

The following compounds of the formula (II) are prepared in a similar manner;

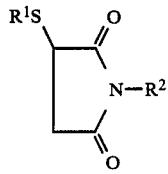
(II)

| No. | $R^1$ | $R^2$ | Physical data [melting point °C.; refractive index $n_D^{20}$ |
|-----|-------|-------|---|
| A2 | i-$C_3H_7$ | 4-$CF_3$—$C_6H_4$— | 122–123 |
| A3 | " | 4-$CF_3$—S—$C_6H_4$— | 95–96 |
| A4 | " | 4-$CH_3$—$C_6H_4$— | 105–107 |
| A5 | " | 2,4-$Cl_2C_6H_3$— | 1.5086 |
| A6 | " | 2-$NO_2$—$C_6H_4$— | 1.5084 |
| A7 | " | 2-Cl—$C_6H_4$— | 1.5047 |
| A8 | " | 2-$CH_3$—$C_6H_4$— | 1.5056 |
| A9 | " | 3-$CH_3$—$C_6H_4$— | 60–62 |
| A10 | " | $C_6H_5$—$CH_2$— | 1.5534 |
| A11 | " | 3-$CF_3$—$C_6H_4$—$CH_2$ | 1.5120 |
| A12 | " | 3-Cl, 4-$CF_3$—$C_6H_3$—$CH_2$ | 1.5398 |
| A13 | n-$C_4H_9$— | 2,6-$(C_2H_5)_2$—$C_6H_3$— | 50–51 |
| A14 | " | 4-$CF_3O$—$C_6H_4$— | 69–73 |
| A15 | " | 3,4-$Cl_2$—$C_6H_3$— | 77–80 |
| A16 | " | 2,4-$Cl_2$—$C_6H_3$— | 1.5725 |
| A17 | " | 2-Cl—$C_6H_4$— | 1.5635 |
| A18 | " | $C_6H_5$—$CH_2$ | 1.5477 |
| A19 | " | 3-$CF_3$—$C_6H_4$—$CH_2$ | 1.5105 |
| A20 | $C_6H_{11}$— | 4-$CF_3$—$C_6H_4$ | 144–145 |
| A21 | " | 4-$CH_3$—$C_6H_4$ | 112–114 |
| A22 | " | 3-Cl—$CH_2$—$CF_2O$—$C_6H_4$ | 1.5260 |
| A23 | " | 2-$CF_3O$—$C_6H_4$ | 1.5260 |
| A24 | " | 4-$CF_3O$—$C_6H_4$ | 125–127 |
| A25 | " | 4-$CF_2ClO$—$C_6H_4$ | 111–113 |
| A26 | " | 3-Cl, 4-$CF_3O$—$C_6H_3$ | 76–78 |
| A27 | " | 2,4-$(CF_3)_2$—$C_6H_3$ | 1.5143 |
| A28 | " | 3-$CF_3O$—$C_6H_4$ | 57–59 |
| A29 | " | 2-$CF_3$—$C_6H_4$ | 1.5345 |
| A30 | i-$C_3H_7$ | $C_6H_{11}$ | oily IR 1.685 cm |
| A31 | " | i-$C_4H_9$ | oily 1.690 cm |

It is understood that the specification and examples are illustrative but not limitative of the present invention and that other embodiments within the spirit and scope of the invention will suggest themselves to those skilled in the art.

We claim:

1. A process for the preparation of a 3-sulphenyl-maleimide of the formula

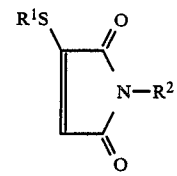

in which
$R^1$ is alkyl, or optionally substituted cycloalkyl or aralkyl, and
$R^2$ is optionally substituted alkyl, cycloalkyl, aryl or aralkyl,
comprising reacting a 3-sulphenylsuccinimide of the formula

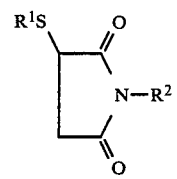

with an equimolar amount of hydrogen peroxide in the presence of a lower alkanecarboxylic acid as a solvent.

2. A process according to claim 1, in which
$R^1$ is alkyl with 1 to 12 carbon atoms, optionally substituted cycloalkyl with 5 to 10 carbon atoms or aralkyl with 1 to 4 carbon atoms in the alkyl part, the aryl part having 6 to 10 carbon atoms and being optionally substituted by halogen, alkyl with 1 to 4 carbon atoms, alkoxy with 1 to 4 carbon atoms, alkylthio with 1 to 4 carbon atoms, halogenoalkyl, halogenoalkoxy and halogenoalkylthio with in each case 1 to 3 carbon atoms and 1 to 5 halogen atoms and/or nitro; and
$R^2$ is alkyl with 1 to 12 carbon atoms, optionally substituted cycloalkyl with 5 to 19 carbon atoms, aralkyl with 1 to 4 carbon atoms in the alkyl part, the aryl part having 10 carbon atoms and being optionally substituted aryl with 6 to 10 carbon atoms, the optional substituents in the aryl part of the aralkyl or in the aryl itself being halogen, alkyl with 1 to 4 carbon atoms, alkoxy with 1 to 4 carbon atoms, alkylthio with 1 to 4 carbon atoms, halogenoalkyl, halogenoalkoxy or halogenoalkylthio with in each case 1 to 3 carbon atoms and 1 to 5 halogen atoms or nitro.

3. A process according to claim 1, wherein the lower alkanecarboxylic acid is formic acid, acetic acid or propionic acid.

4. A process according to claim 1, wherein the reaction is effected at a temperature between about 20° and 120° C.

* * * * *

UNITED STATES PATENT AND TRADEMARK OFFICE
CERTIFICATE OF CORRECTION

PATENT NO. : 4,874,874

DATED : October 17, 1989

INVENTOR(S) : Kuhle et al.

It is certified that error appears in the above-identified patent and that said Letters Patent is hereby corrected as shown below:

Title Page  Heading:  Delete " Kule et al " and substitute -- Kuhle --

Title Page  [75] Inventors:  Delete " Kule " and substitute --Kuhle --

Signed and Sealed this

Second Day of July, 1991

Attest:

HARRY F. MANBECK, JR.

Attesting Officer

Commissioner of Patents and Trademarks